United States Patent [19]

Meiattini

[11] Patent Number: 5,128,265
[45] Date of Patent: Jul. 7, 1992

[54] REAGENT USEFUL FOR DETECTION AND QUANTITATIVE DETERMINATION OF LEUKOCYTES IN BIOLOGICAL FLUIDS

[75] Inventor: Franco Meiattini, Siena, Italy

[73] Assignee: Diesse Diagnostica Senese S.r.l., Milan, Italy

[21] Appl. No.: 546,763

[22] Filed: Jul. 2, 1990

[30] Foreign Application Priority Data

Sep. 21, 1989 [IT] Italy .................. 21788 A/89

[51] Int. Cl.$^5$ ............................. G01N 33/49
[52] U.S. Cl. ........................ 436/17; 436/18; 436/904; 252/700
[58] Field of Search ............ 436/6, 17, 18, 63, 66, 436/166, 71, 904; 435/4, 14, 11, 28; 252/700

[56] References Cited

U.S. PATENT DOCUMENTS

| | | | |
|---|---|---|---|
| 3,087,794 | 4/1963 | Free et al. | 435/28 |
| 3,886,045 | 5/1975 | Meiattini | 435/28 X |
| 4,295,853 | 10/1981 | Kasahara et al. | 436/66 |
| 4,721,670 | 1/1988 | Osada et al. | 435/28 |
| 4,755,472 | 7/1988 | Ismail et al. | 436/66 |
| 4,851,353 | 7/1989 | Miike et al. | 435/28 X |

FOREIGN PATENT DOCUMENTS

121317 10/1984 European Pat. Off. .

OTHER PUBLICATIONS

Tomankova, H. et al. "The Oxidation of Aminophenazone by Hydrogen Peroxide" Microchemical Journal, vol. 20, 132–153 (1975).
Bos, A. J. et al. "Some Enzymatic Characteristics of Eosinophil Peroxidase from Patients with Eosinophilia and from Healthy Donors." Infection and Immunity, vol. 32, No. 2, 1981, pp. 427–431.
Meiattini, F. et al. "The 4-Hydroxybenzoate/4-Aminophenazone Chromogenic System Used in the Enzymic Determination of Serum Cholesterol." Clinical Chemistry, vol. 24, No. 12, 1978, pp. 2161–2165.
Cowman, R. A. "Evidence for Thiocyanate-Sensitive Peroxidase Activity in Human Saliva." Journal of Clinical Microbiology, vol. 18, No. 5, 1983, pp. 1177–1182.
Matheson, N. R. "Isolation and Properties of Human Neutrophil Myeloperoxidase." Biochemistry, vol. 20, 1981, pp. 325–330.

Primary Examiner—James C. Housel
Assistant Examiner—Jeffrey R. Snay
Attorney, Agent, or Firm—Oblon, Spivak, McClelland, Maier & Neustadt

[57] ABSTRACT

A reagent for the detection and quantitative determination of leukocytes by measuring the myeloperoxidase (MPO) activity of biological samples, which is sensitive for disclosing even only a few leukocytes, without interferences caused by hemoglobin even in the presence of several erythrocytes, and suitable for photometric readings in the visible spectrum region. The reagent comprises a buffer, a chromogen, a surface-active agent, at least an alkali metal halide, a hydroperoxide compound and optionally a reaction promoter.

10 Claims, No Drawings

REAGENT USEFUL FOR DETECTION AND QUANTITATIVE DETERMINATION OF LEUKOCYTES IN BIOLOGICAL FLUIDS

BACKGROUND OF THE INVENTION

1. Field of the Invention:

The present invention refers to a reagent for the detection and quantitative determination of leukocytes in samples of human and animal body fluids, and to a method of using it.

The detection of leukocytes in body fluids, such as, e.g., urine, is very useful in the diagnosis of some types of infections, e.g. in the uro-genital tract.

2. Discussion of the Background

For the detection of leukocytes in the urine two different methods are at present employed: the microscopic examination and the determination of particular enzyme activities which can be correlated with the pressure of leukocytes themselves.

The microscopic examination of sample represents the classical method for detecting leukocytes and is considered as the reference method in that it allows the objective control of the presence of the cells (leukocytes) in the test sample, directly or after enrichment by centrifugation. However, such a method, besides being too laborious for extensive utilization in analysis laboratories, does not allow the indentification of leukocyte cells having undergone lysis caused by excessive alkalinity of sample or a too wide time interval elapsed from the taking of the sample and its microscopic examination, which represents a serios drawback. For strongly alkaline samples, as it often happens in case of infection of urinary ducts, cell lysis can reach completion even within one hour. Under such circumstances, the risk of considering as negative samples, which are on the contrary positive, is very high.

Esterases are the enzymes at present employed for the indirect detection of leukocytes, in that they split particular synthetic substrates by hydrolysis delivering groups which spontaneously become coloured by air oxidation of after reaction with other appropriate substances. This method is th one typically employed in reactive stripes which contain the reagents dried on inert supports and are used for detection of leukocytes in urine. The reaction stripes containing the dried reagents to be dipped in the test sample allow a semi-quantitative determination of leukocyte esterase activity, which requires a time period of at least 60-120 seconds per sample. The detection of leukocytes carried out through the measurement of peroxidase enzyme activity is also known from a long time. In U.S. Pat. No. 3,087,794 a method is described, which is useful for distinguishing the peroxidase activity of leukocytes from that of erythrocytes. The utilization of hydrogen peroxides (or another peroxide) at different concentrations in the two cases permits such a differentation: o-tolidine, which is a cancerous substance, is the employed chromogen.

The method described in the above-mentioned U.S. Patent, however, does not reach the sensitivity level which are at present requested and is not even able to distiguish leukocytes from erythrocytes with certainty, if the concentration of these latter is much higher than that of the former.

The leukocytes typically present in urine in csae of renal and uro-genital infections are neutrophilic granulocytes.

They have the typical microbicidal function correlated to the phagocytosis, that is carried out through different mechansims, not yet perfectly understood. Among them, the most important one appears to be the microbicidal and detoxicating MPO-$H_2O_2$-halide system. With MPO it is hereinafter meant the leudocyte myleoperoxidase enzyme.

MPO is an enzyme present in large amount in polymorphonuclear leukocytes (neutrophils granulocytes), representing up to 5% of the whole cell mass.

The determination of MPO activity can therefore allow the detection of the presence of the above mentioned leukocytes in biological samples or in human or animal body fluds. When the halide compund in MPO-$H_2O_2$-halide system is iodide ($I^-$), the following reactions can take place:

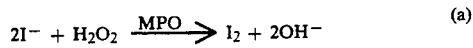   (a)

   (b)

J. Bos et al. (Infect. Immun. 1981, 32, 427) exploy just the reactions (a) and (b) for determining the myeloperoxidase activity of neutrophils and the peroxidase activity of eosinophils in blood, by carrying out spectrophotometric readings at 360 nm of the reaction production ($I_3$). However, the UV spectrophotometric reading involves many practical drawbacks and brings about many non-specificities when applied to samples having extremely variable compositions, such as urine.

Methods are also known for determining the MPO activity in blood, which are comparable to the ones already extensively employed for the peroxidase of vegetable origin (HRPO) and employ o-dianisidine, o-tolidine or guaiacol as acceptor-chromogens. These methods too are however non-specific because they do not distinguish among peroxidase activity, MPO activity and hemoglobin pseudo-peroxidase activity.

SUMMARY OF THE INVENTION

It has now been surprisingly found a reagent suitable both for the detection and for the quantitative determination of leukocytes in biological samples through the measurement of MPO activity, enough sensitive for disclosing even only a few leukocytes, having such a specificity that hemoglobin does not bring about interference at all even in the presence of several erythrocytes and being suitable for photometric readings in the visible spectrum region.

The reagent according to the present invention comprises a MPO specific substrate, such as an alkali metal halide compound; 4-aminoantipyrine as chromogen; a buffer for maintaining the optimum desired pH value; a surface-active agent for aiding and accelerating the lysis of leukocytes in order to release MPO making it immediately avaialble for the reactions of interest; a hydroperoxide compound, and optionally a promoter for increasing the systen sensitivity.

DETAILED DESCRIPTION OF THE PREFERRED EMBODIMENTS

More particularly, such reagent comprises as components at least a buffer selected from the group consisting of citrate, succinate, acetate, and formate in concentration of 2.5-500 mmol/l; a chromogen represented by 4-aminoantipyrine in concentration of 5-1000 mmol/l;

at least a surface-active agent selected from the group formed by non-ionic and anionic surface-active agents, in concentration of 0.05-2%; at least an alkali metal halide in concentration of 2-1000 mmol/l; and at least a hydroperoxide compound in concentration of 2-100 mmol/l.

Preferably the buffer is in concentration of 2.5-50 mmol/l; the chromogen is in a concentration of 200-500 mmol/l; the surface-active agent is in concentration of about 0.2% the alkali metal halide is in a concentration of 10-20 mmol/l; and the hydroperoxide compound is selected from the group consisting of hydrogen peroxide in a concentration of about 2-25 mmol/l and magnesium monoperoxyphthalate in a concentration of about 40-60 mmol/l.

Hydroperoxide compunds other than hydrogen peroxide and magensium monoperoxyphtalate can be used, such as urea hydrogen peroxide, both alone and in mixture with each other in the reagent. Substances such as MPO (3-(N-morpholine)propane-sulfonic acid), imidaxole and/or 8-aminoquinoline, in concentrations from 10-300 mmol/l can be present, for increasing the reagent sensitivity.

Expecially 8-aminoquinoline can bring about a clear promoting effect, preferably in concentration of 30-40 mmol/l so as to increase reaction sensitivity.

The reaction involved by the chromogen activity is considered to be as follows:

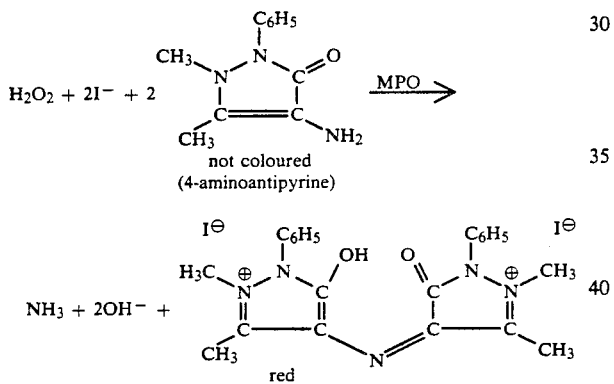

not coloured
(4-aminoantipyrine)

red

The reaction rate which can be achieved for the detection and quantatitive determination of leukocytes allows the examination of the sample in about 30 seconds when the components are used in the above specified optimum amounts; if said components are used in amounts which are not the optimum ones but falling within the indicated ranges, an effective detection and quantitative determination of the leukocytes is still effectively possible even if the operating time is longer. For the practical utilization of reagent and method according to the present invention the essential thin is a conventional filter photometer for readings in the visible spectrum region, even if the utilization of more comples and sophisticated instruments, particularly suitable for automation and acceleration of analytical procedures cannot be excluded.

The reagent of the present invention can be employed when its components are included in only one or even in two compartment parts.

When the reagent is used in an only component part containing all the above-mentioned components, it is necessary to do the detection and quantitative determination of leukocytes quickly with precision because the components immediately react with the biological substrate; the components of the reagent can also be split into two component parts which are, one after the other, let to react with the biological fluids. A component part can in fact include the alkali metal halide and the other part the hydroperoxide compund, the remaining components being included in one or both component parts, except chromogen being only in the component part that is first added to the biological fluid sample.

The chromogen 4-aminoantipyrine allows a coloured oxidized compound to be formed, its colour intensity being such as to allow the determination of MPO activity by means of spectrophotometric readings in the visible spectrum region (520-540 nm) with sufficient sensitivity and specificity.

The alkali metal halide, preferably potassium iodide, is used as MPO specific substrate in the reagent.

The buffers preferably used are citrate (because it gives more stability to the reagent) or formate (because it increases reaction sensitivity).

In order to accelerate the leukocyte lysis for releasing MPO and making it immediately available for the reaction of interest, 0.1-2%, preferably about 0.2%, of a nonionic surface-active agent, such as polyoxyethylene(20 )sorbitan monolaurate (Tween 20®), polyoxyethylene(20)-sorbitan monoleate (Tween 80®), polyxyethylene(23)lauryl ether (Brij 35®), higher alcohol polyoxyethylene ethers (Triton x-67®; Triton x-100®; Triton x-305®), preferably polyethylene glycol p-isooctylphenyl ether (Triton x-10$^2$®) can suitably be added to the reagent.

The following Examples as illustrative, but not limitative of the present invention.

EXAMPLES

EXAMPLE 1

A reagent is prepared formed by a first component part, consisting of citrate buffere (196 mmol/l, pH 5.0) containing 4-aminoantipyrine (62 mmol/l), potassium iodide (130 mmol/l), 8-aminoquionoline (28 mmol/l) and Triton x-100® (10 g/l), and by a second component part, consisting of hydrogen peroxide (20 mmol/l) in distilled water.

In a spectrophotometry cuvette, thermoregulated at 37° C. and having 1 cm of optical path, are successively mixed: 2.0 ml of distilled water and 0.5 ml of a fresh urine sample containing varied amounts of leukocytes, previously measured by microscopic counting of the sediment obtained by centrifugation of the sample.

After addition of 0.5 ml of the first component part, the absorbance ($A_1$) at 540 nm is measured and then 0.1 ml of the second component part is added.

The resulting mixture has pH 5.0. Exactly 30 seconds after the addition of the second component part, the absorbance ($A_2$) at 540 nm is measured.

The calculated absorbance variation ($A_2 - A_1$) obtained in 30 seconds is then correlated with the leukocyte content of the sample. The obtained results are summarized in Table I.

TABLE I

| Leukocytes per μl | ($A_2 - A_1$) |
|---|---|
| 0 | 0.036 |
| 0 | 0.042 |
| 0 | 0.028 |
| 0 | 0.040 |
| 25 | 0.070 |

TABLE I-continued

| Leukocytes per μl | $(A_2 - A_1)$ |
|---|---|
| 25 | 0.070 |
| 25-30 (28) | 0.078 |
| 75 | 0.085 |
| 75-80 (78) | 0.092 |
| 500 | 0.702 |
| 700 | 0.908 |

Leukocytes per μl: number of leukocytes per μl of fresh urine, measured by microscopic counting of the sediment obtained by centrifugation of the sample.
$(A_2 - A_1)$: Absorbance variation obtained in 30 seconds.

Example 2

The same procedure of Example 1 is repeated, with the exception that the reagent consists of a first component part, containing succinate buffer (20 mmol/l, pH 7.2), 4-aminoantipyrine (62 mmol/l), potassium iodide (130 mmol/l), 8-aminoquinoline (28 mmol/l), and Triton x-100 ® (20 g/l), and of a second component part, containing hydrogen peroxide (20 mmol/l) in citrate buffer (100 mmol/l, pH 4.7).

The resulting mixture has the same pH 5.0 as the Example 1, not withstanding the different pH of the compositions. The calculated absorbance variation $(A_2 - A_1)$ obtained in 30 seconds is correlated with the leukocyte content of the sample.

The obtained results are summarized in Table II.

TABLE II

| Leukocytes per μl | $(A_2 - A_1)$ |
|---|---|
| 0 | 0.040 |
| 0 | 0.044 |
| 0 | 0.032 |
| 0 | 0.040 |
| 25 | 0.081 |
| 25 | 0.078 |
| 25-30 (28) | 0.078 |
| 75 | 0.092 |
| 75-80 (78) | 0.093 |
| 500 | 0.775 |
| 700 | 1.010 |

Leukocytes per μl: number of leukocytes per μl of fresh urine, measured by microscopic counting of the sediment obtained by centrifugation of the sample.
$(A_2 - A_1)$: Absorbance variation obtained in 30 seconds.

Example 3

In a spectrophotometry cuvette, thermoregulated at 37° C. and having 1 cm of optical path, are successively mixed: 2.0 ml of distilled water and 0.5 ml of a fresh urine sample composed by a mixture of a group of negative urines or by a mixture of a group of positive urines containing 200 leukocytes/ul, determined by microscopic counting in the sediment obtained by centrifugation of the sample.

After addition of 0.5 ml of the reagent first component part consisting of acetate buffer (100 mmol/l, pH 4.8) containing 4-aminoantipyrine (40 mmol/l), 8-aminoquinoline (25 mmol/l), Triton X-100 ® (15 g/l) and potassium iodide in concentrations ranging between 100 and 175 mmol/l, the absorbance $(A_1)$ at 530 nm is measured and then 0.1 ml of the second component part, consisting of hydrogen peroxide (20 mmol/l), is added. Exactly 30 seconds after the addition, the absorbance $(A_2)$ at 530 nm is measured. The calculated absorbance variation $(A_2 - A_1)$ in 30 seconds is correlated with the iodide concentration.

The obtained results are summarized in Table III.

TABLE III

| Iodide mmol/l | | N | P | (P − N) |
|---|---|---|---|---|
| in the reagent | in the cuvette | | | |
| 100 | 16.12 | 0.032 | 0.211 | 0.179 |
| 125 | 20.16 | 0.048 | 0.320 | 0.272 |
| 150 | 24.80 | 0.098 | 0.388 | 0.290 |
| 175 | 28.22 | 0.148 | 0.387 | 0.239 |

$N = (A_2 - A_1)$ at 530 nm per 0.5 ml of a sample of the group of negative urines
$P = (A_2 - A_1)$ at 530 nm per 0.5 ml of a sample of the group of positive urines
$(P - N)$ = difference between the $(A_2 - A_1)$ values of the positive sample and those of the negative sample.

Example 4

The same procedure of Example 3 is repeated, with the exception that, in this case the reagent comprises a first component part, consisting of acetate buffer (100 mmol/l, pH 4.8) containing 4-aminoantipyrine (40 mmol/l), 8-aminoquinoline (25 mmol/l), Triton X-305 ® (20 g/l) and hydrogen peroxide in concentrations ranging from 5 to 7 mmol/l, and a second component part, consisting of potassium iodide (600 mmol/l), and the following results are obtained, as reported in Table IV.

TABLE IV

| Peroxide mmol/l | | N | P | (P − N) |
|---|---|---|---|---|
| in the Reagent | in the cuvette | | | |
| 5 | 0.81 | 0.048 | 0.410 | 0.362 |
| 6 | 0.96 | 0.105 | 0.460 | 0.355 |
| 7 | 1.13 | 0.180 | 0.500 | 0.320 |

$N = (A_2 - A_1)$ at 530 nm per 0.5 ml of a sample of the group of negative urines
$P = (A_2 - A_1)$ at 530 nm per 0.5 ml of a sample of the group of positive urines
$(P - N)$ = difference between the $(A_2 - A_1)$ values of the positive sample and those of the negative sample.

Example 5

The same procedure of Example 3 is repeated, whith the exception that, in this case, the reagent comprises a first component part, consisting of acetate buffer (100 mmol/l), 8-aminoquinoline (25 mmol/l), potassium iodide (140 mmol/l), Triton X-67 ® (2.5 g/l) and 4-aminoantipyrine in concentrations ranging from 40 to 320 mmol/l, and a second component part, consisting of hydrogen peroxide (25 mmol/l) in citrate buffer (100 mmol/l, pH 4.8). The employed samples are formed by a mixture of a group of negative urines and by a mixture of a group of positive urines containing 70 and 250 leukocytes/ul, measured by microscopic counting of the sediment obtained by centrifugation of the sample.

The obtained results are summarized in Table V.

TABLE V

| 4-aminoantipirine mmol/l | | N | P70 | P250 |
|---|---|---|---|---|
| In the reagent | in the cuvette | | | |
| 40 | 6.45 | 0.048 | 0.142 | 0.488 |
| 80 | 12.90 | 0.060 | 0.145 | 0.512 |
| 120 | 19.35 | 0.058 | 0.140 | 0.470 |
| 160 | 25.81 | 0.056 | 0.148 | 0.465 |
| 320 | 51.61 | 0.045 | 0.150 | 0.413 |

$N = (A_2 - A_1)$ at 530 nm per 0.5 ml of a sample of the group of negative urines
$P70 = (A_2 - A_1)$ at 530 nm per 0.5 ml of a sample of the group of positive urines containing 70 leukocytes/μl
$P250 = (A_2 - A_1)$ at 530 nm per 0.5 ml of a sample of the group of positive urines containing 250 leukocytes/μl

Example 6

In a spectrophotometry cuvette, having 1 cm of optical path and thermoregulated at 37° C., are successively mixed: 2.0 ml of distilled water and 0.5 ml of a fresh urine sample formed by a mixture of a group of negative urines or by a mixture of a group of positive urines containing 250 leukocytes/ul, measured by microscopic counting of the sediment obtained by centrifugation of the sample.

After the addition of 0.5 ml of a first component part of the reagent, consisting of acetate buffer (100 mmol/l, pH 4.8) containing 4-aminoantipyrine (40 mmol/l), potassium iodide (140 mmol/l), Tween-20® (10 g/l) and 8-aminoquinoline in concentrations ranging from 15 to 40 mmol/l, the absorbance ($A_1$) at 530 nm is measured and then 0.1 ml of a second component part of the reagent, consisting of magnesium monoperoxyphthalate (50 mmol/l), is added. The calculated absorbance variation ($A_2 - A_1$) in 30 seconds is correlated with the concentration of 8-aminoquinoline. The obtained results are summarized in Table VI.

TABLE VI

| 8-Aminoquinoline mmol/l | | N | P | (P − N) |
|---|---|---|---|---|
| in the reagent | in the vessel | | | |
| 15 | 2.42 | 0.041 | 0.405 | 0.364 |
| 20 | 3.23 | 0.045 | 0.460 | 0.415 |
| 30 | 4.84 | 0.047 | 0.458 | 0.411 |
| 40 | 6.45 | 0.051 | 0.461 | 0.410 |

N = ($A_2 - A_1$) at 530 nm per 0.5 ml of a sample of the group of negative urines
P = ($A_2 - A_1$) at 530 nm per 0.5 ml of a sample of the group of positive urines
(P − N) = difference between the ($A_2 - A_1$) values of the positive sample and those of the negative sample.

Example 7

In a spectrofotometry cuvette, having 1 cm of optical path and thermoregulated at 37° C., are mixed successively 2.0 ml of distilled water and 0.5 ml of a fresh urine sample containing varied amounts of leukocytes, measured by microscopic counting of the sediment obtained by centrifugation of the sample.

After the addition of 0.5 ml of the first component part of the reagent, consisting of citrate buffer (175 mmol/l, pH 4.8) containing 4-aminoantipyrine (50 mmol/l), potassium iodide (120 mmol/l) and Tween-80® (10 g/l), the absorbance ($A_1$) at 540 nm is measured in two series of tests carried out in the presence or not of 8-aminoquinoline as promoter (31 mmol/l) in the first component part.

Then, 0.1 ml of a second component part of the reagent, consisting of hydrogen peroxide (25 mmol/l) in citrate buffer (100 mmol/l, pH 4.8) is added. Exactly 30 seconds after the addition, the absorbance ($A_2$) at 540 nm is measured. The calculated absorbance variation ($A_2 - A_1$) in 30 seconds is correlated with the leukocyte content of the sample sediment; the obtained results are summarized in Table VII.

TABLE VII

| | ($A_2 - A_1$) | |
|---|---|---|
| Leukocytes per μl | Reagent without promoter | Reagent with promoter |
| 0 (Negative) | 0.025 | 0.040 |
| 25 | 0.050 | 0.085 |
| 50 | 0.065 | 0.110 |
| 100 | 0.150 | 0.223 |
| 200 | 0.220 | 0.370 |
| 300 | 0.345 | 0.580 |

($A_2 - A_1$): absorbance variation in 30 seconds
Leukocytes per μl = Number of leukocytes per μl of fresh urine measured by microscopic counting of the sediment obtained by centrifugation of the sample.

Example 8

In a spectrophotometry cuvette having 1 cm of optical path and thermoregulated at 37° C., are mixed successively: 2.0 ml of distilled water and 0.5 ml of a urine sample formed by a mixture of a group of negative urines or by a mixture of a group of positive urines containing 250 leukocytes/ul, measured by microscopic counting of the sediment obtained by centrifugation of the sample.

After addition of 0.5 ml of the first component part of the reagent, consisting of citrate buffer (100 mmol/l) at pH ranging from 4.0 to 7.0 and containing 4-aminoantipyrine (40 mmol/l), potassium iodide (140 mmol/l), 8-aminoquinoline (25 mmol/l) and Triton X-100® (15 g/l), the absorbance ($A_1$) at 530 nm is measured, 0.1 ml of a second component part of the reagent, consisting of hydrogen peroxide (25 mmol/l) in distilled water, is then added and, exactly 30 seconds after the addition of this latter, the absorbance ($A_2$) at 530 nm is measured.

The obtained results are summarized in Table VIII.

TABLE VIII

| | ($A_2 - A_1$) | | |
|---|---|---|---|
| pH | N | P | (P − N) |
| 4.0 | 0.050 | 0.061 | 0.011 |
| 4.5 | 0.037 | 0.400 | 0.363 |
| 4.8 | 0.045 | 0.415 | 0.370 |
| 5.0 | 0.044 | 0.408 | 0.364 |
| 5.5 | 0.047 | 0.368 | 0.321 |
| 6.0 | 0.038 | 0.288 | 0.250 |
| 6.5 | 0.010 | 0.120 | 0.110 |
| 7.0 | 0.012 | 0.012 | 0.000 |

N = ($A_2 - A_1$) at 530 nm per 0.5 ml of a sample of the group of negative urines
P = ($A_2 - A_1$) at 530 nm per 0.5 ml of a sample of the group of positive urines
(P − N) = difference between the ($A_2 - A_1$) values of the positive sample and those of the negative sample.

Example 9

In a spectrophotometry cuvette having 1 cm of optical path and thermoregulated at 37° C., are mixed successively 1.6 ml of distilled water, 0.5 ml of fresh urine sample containing leukocytes or erythrocytes in known varied amounts, determined by microscopic counting of the sediment obtained by centrifugation of the sample, and 0.5 ml of the first component part of the reagent, consisting of citrate buffer (20 mmol/l, pH 7.2) containing 4-aminoantipyrine (62 mmol/l), potassium iodide (132 mmol/l) and Brij-35® (2 g/l). The absorbance ($A_1$) at 530 nm is measured and then 0.5 ml of a second component part of the reagent, containing citrate buffer (200 mmol/l, pH 4.4), hydrogen peroxide (6.0 mmol/l) and 8-aminoquinoline (30 mmol/l) are added.

Exactly after 30 seconds after the addition of second component part, the absorbance ($A_2$) at 530 nm is measured. The calculated absorbance variation ($A_2 - A_1$) is correlated with the leukocyte or erythrocyte content of the sample. The obtained results are summarized in Table IX.

TABLE IX

| Leukocytes/μl | Erythrocytes/μl | ($A_2 - A_1$) |
|---|---|---|
| 0 | 0 | 0.035 |
| 0 | 0 | 0.044 |
| 15 | 0 | 0.058 |
| 20 | 0 | 0.068 |
| 35 | 0 | 0.102 |
| 250 | 0 | 0.399 |
| 0 | 10 | 0.038 |
| 0 | 50 | 0.036 |
| 0 | 250 | 0.042 |

TABLE IX-continued

| Leukocytes/µl | Erythrocytes/µl | $(A_2 - A_1)$ |
|---|---|---|
| 0 | 500 | 0.040 |

$(A_2 - A_1)$: Absorbance variation after 30 seconds.

Example 10

In a spectrophotometry cuvette, having 1 cm of optical path and thermoregulated at 37° C., are mixed successively 1.6 ml of distilled water, 0.5 ml of a fresh urine sample containing leukocytes and erythrocytes in known varied amounts, determined by microscopic counting of the sediment obtained by centrifugation of the sample, and 0.5 ml of the first component part of the reagent, consisting of formate buffer (20 mmol/l, pH 7.1) containing 4-aminoantipyrine (120 mmol/l), potassium iodide (130 mmol/l) and Triton x-100 ® (2 g/l); the absorbance ($A_1$) at 530 nm is measured and then 0.1 ml of a second component part of the reagent, consisting of a buffer (300 mmol/l pH 4.4) of a compound selected from citrate, formate succinate or acetate, containing hydrogen peroxide (5.7 mmol/l) and 8-aminoquinoline (31 mmol/l) are added.

Exactly 30 seconds after the addition of the second component part, the absorbance ($A_2$) at 530 nm is measured.

The calculated absorbance variation ($A_2 - A_1$) is correlated with the leukocyte or erythrocyte content of the sample.

The obtained results are summarized in Table X.

TABLE X

| Leuko-cytes/µl | Erythro-cytes/µl | $(A_2 - A_1)$ Reagent with citrate | Reagent with formate | Reagent with succinate | Reagent with acetate |
|---|---|---|---|---|---|
| 0 | 0 | 0.034 | 0.048 | 0.046 | 0.039 |
| 0 | 0 | 0.038 | 0.049 | 0.044 | 0.037 |
| 15 | 0 | 0.059 | 0.074 | 0.068 | 0.062 |
| 25 | 0 | 0.081 | 0.107 | 0.090 | 0.085 |
| 75 | 0 | 0.164 | 0.210 | 0.187 | 0.190 |
| 500 | 0 | 0.872 | 1.204 | 0.920 | 0.898 |
| 0 | 10 | 0.032 | 0.061 | 0.059 | 0.042 |
| 0 | 50 | 0.041 | 0.055 | 0.058 | 0.038 |
| 0 | 250 | 0.039 | 0.057 | 0.054 | 0.038 |
| 0 | 500 | 0.044 | 0.057 | 0.060 | 0.039 |
| 0 | 1000 | 0.052 | 0.066 | 0.062 | 0.051 |

$(A_2 - A_1)$: Absorbance variation after 30 seconds

Example 11

In a spectrophotometry cuvette, having 1 cm of optical path and thermoregulated at 37° C., are mixed successively; 2.0 ml of distilled water, 0.5 ml of a fresh urine sample formed by a mixture of a group of negative urines or by a mixture of a group of positive urines containing 250 leukocytes/ul, measured by microscopic counting of the sediment obtained by centrifugation of the sample, and 0.5 ml of the reagent consisting of succinate buffer (100 mmol/l, pH 4.8) containing 4-aminoantipyrine (123 mmol/l), potassium iodide (132 mmol/l), 8-aminoquinoline (31 mmol/l); hydrogen peroxide (6 mmol/l) and varied surface-active agents (3.0 g/l). The absorbance at 520 nm is measured immediately ($A_1$) and exactly after 30 seconds ($A_2$).

In table XI are summarized the obtained results.

TABLE XI

| Surface-active agent | $(A_2 - A_1)$ N | P | (P - N) |
|---|---|---|---|
| None | 0.033 | 0.092 | 0.059 |
| Teepol 610 ® | 0.018 | 0.088 | 0.070 |
| Litium dodecyl sulfate | 0.008 | 0.118 | 0.110 |
| Sodium dodecyl sulfate | 0.011 | 0.099 | 0.088 |
| Sodium dioctylsulphosuccinate | 0.011 | 0.069 | 0.058 |
| Sodium pentanesulfonate | 0.019 | 0.110 | 0.091 |
| Sodium hexanesulfonate | 0.018 | 0.106 | 0.088 |
| Brij 35 ® | 0.032 | 0.420 | 0.388 |
| Triton x-67 ® | 0.048 | 0.502 | 0.454 |
| Triton x-100 ® | 0.041 | 0.496 | 0.455 |
| Triton x-305 ® | 0.037 | 0.377 | 0.340 |
| Tween 20 ® | 0.035 | 0.501 | 0.466 |
| Tween 80 ® | 0.023 | 0.491 | 0.468 |

N = $(A_2 - A_1)$ at 520 nm per 0.5 ml of a sample of the group of negative urines.
P = $(A_2 - A_1)$ at 520 nm per 0.5 ml of a sample of the group of positive urines.
(P - N) = difference between the $(A_2 - A_1)$ values of the positive sample and those of the negative sample.

Example 12

In a spectrophotometric cuvette, having 1 cm of optical path and thermoregulated at 37° C., are mixed successively; 2.0 ml of distilled water, 0.8 ml of a fresh urine sample containing varied amounts of leukocytes, previously measured by microscopic counting of the sediment obtained by centrifugation of the sample, and 0.5 ml of the first component part of the reagent, consisting of citrate buffer (5 mmol/l, ph 8.0) containing 4-aminoantipyrine (400 mmol/l), potassium iodide (14.5 mmol/l) and Triton x-100 ® (2 g/l) in distilled water; after the addition of 0.5 ml of the second component part of the reagent, consisting of citrate buffer (266 mmol/l), ph 4.4), hydrogen peroxide (18 mmol/l), and 8-aminoquinoline (31 mmol/l) in dimethylsulfoxide (112 ml/l) in distilled water, the variation of absorbance ($A_2 - A_1$) is misured at 546 nm for 20 sec. The calculated absorbance variation ($A_2 - A_1$) is correlated with the leukocyte contents of the sample.

The obtained results are summarized in Table XII.

TABLE XII

| LEUKOCITES per ul | $(A_2 - A_1)$ |
|---|---|
| 0 | 0.038 |
| 0 | 0.036 |
| 0 | 0.027 |
| 10-15 | 0.045 |
| 20 | 0.049 |
| 25 | 0.055 |
| 25-30 | 0.059 |
| 70-80 | 0.082 |
| 100-130 | 0.110 |
| 600 | 0.398 |
| 900 | 0.588 |

$(A_2 - A_1)$: Absorbance variation for 20 seconds.

I claim:

1. A reagent for detection and quantitative determination of leukocytes in biological fluids by photometric reading in the visible spectrum region, consisting essentially of (i) a buffer selected from the group consisting of citrate, succinate, acetate and formate in a concentration of 25-500 mmol/l; (ii) a 4-aminoantipyrine chromogen in a concentration of 5-1000 mmol/l; (iii) a non-ionic surface-active agent, in a concentration of 0.05-2% wt/vol; (iv) an alkali metal halide in a concentration of 2-1000 mmol/l; (v) and a hydroperoxide compound in a concentration of 2-100 mmol/l.

2. The reagent of claim 1, wherein said surface active agent is at least one member selected from the group consisting of polyoxyethylene (20) sorbitan monlaurate, polyoyethylene(20)sorbitan monoleate, polyoxyethylene(23)lauryl ether and high alcohol polyoxyethylene ethers.

3. The reagent according to claim 1, wherein said hydropeeroxide compound is selected from the group consisting of hydrogen peroxide, mangesium monperoxyphthalate and urea hydrogen peroxide.

4. The reagent according to claims 1 or 3, wherein said alkali metal halide is potassium iodide.

5. The reagent according to claims 1 or 3, wherein the surface-active agent is a higher alcohol polyoxyethylene ether.

6. The reagent of claim 5, wherein the surface-active agent is polyethylene glycol p-isoctylphenyl ether.

7. The reagent according to claims 1 or 3, which further comprises a promoter selected from the group consisting of 3-(N-morpholino)-propanesulfonic acid, 8-aminoquinoline and imidazole, in a concentration of 10-300 mmol/l.

8. The reagent according to claim 7, wherein the promoter is 8-aminoquinoline in a concentration of 30-40 mmol/l.

9. The reagent according to claim 3, wherein the buffer is in a concentration of 2.5-50 mmol/l, the chromogen is in a concentration of 200-500 mmol/l; the surface active agent is in a concentration of about 0.2% wt/vol.; the alkali metal halide is in a concentraton of 10-20 mmol/l; said hydrogen peroxide compound is selected from the group consisting of hydrogen peroxide in a concentration of about 5-25 mmol/l and magnesium monoperoxyphthalate in a concentration of about 40-60 mmol/l.

10. The reagent according to claims 1 or 9, wherein said buffer is citrate or formate.

* * * * *